(12) United States Patent
Shao et al.

(10) Patent No.: US 11,874,261 B2
(45) Date of Patent: Jan. 16, 2024

(54) METHOD AND INTERNET OF THINGS (IOT) SYSTEM FOR MANAGING DUST POLLUTION IN SMART CITY

(71) Applicant: CHENGDU QINCHUAN IOT TECHNOLOGY CO., LTD., Sichuan (CN)

(72) Inventors: Zehua Shao, Chengdu (CN); Haitang Xiang, Chengdu (CN); Yong Li, Chengdu (CN); Yaqiang Quan, Chengdu (CN); Xiaojun Wei, Chengdu (CN)

(73) Assignee: CHENGDU QINCHUAN IOT TECHNOLOGY CO., LTD., Chengdu (CN)

( * ) Notice: Subject to any disclaimer, the term of this patent is extended or adjusted under 35 U.S.C. 154(b) by 0 days.

(21) Appl. No.: 17/804,092

(22) Filed: May 25, 2022

(65) Prior Publication Data

US 2023/0324352 A1   Oct. 12, 2023

(30) Foreign Application Priority Data

Apr. 6, 2022 (CN) .......................... 202210352984.4

(51) Int. Cl.
*G01N 33/00* (2006.01)
*G06Q 50/26* (2012.01)
*G16Y 40/10* (2020.01)
*G16Y 20/10* (2020.01)

(52) U.S. Cl.
CPC ......... *G01N 33/0004* (2013.01); *G06Q 50/26* (2013.01); *G16Y 20/10* (2020.01); *G16Y 40/10* (2020.01)

(58) Field of Classification Search
CPC ............................... G06Q 50/26; G16Y 40/10
See application file for complete search history.

(56) References Cited

U.S. PATENT DOCUMENTS

| 2018/0178781 | A1* | 6/2018 | Funk | ........................ H04L 67/12 |
| 2019/0154538 | A1* | 5/2019 | Solomon | ................. G01M 3/00 |
| 2022/0092418 | A1 | 3/2022 | Liu et al. | |

FOREIGN PATENT DOCUMENTS

| CN | 104318315 | A | | 1/2015 |
| CN | 109887282 | | * | 6/2019 |

(Continued)

OTHER PUBLICATIONS

Notification to Grant Patent Right for Invention in Chinese Application No. 202210352984.4 dated May 27, 2022, 7 pages.

(Continued)

*Primary Examiner* — Jamel E Williams
*Assistant Examiner* — Alex T Devito
(74) *Attorney, Agent, or Firm* — METIS IP LLC

(57) ABSTRACT

The embodiments of the present disclosure provide a method and an Internet of Things (IoT) system for managing dust pollution in a smart city. The method may be executed by a management platform, the method may include: obtaining one or more environmental data of the area to be detected through the sensing network platform, and obtaining one or more street data associated with the environmental data, the environmental data at least including dust data indicating dust information in the air; determining whether there is dust pollution in the area to be detected based on the environmental data; and in response to the determining that there is dust pollution in the area to be detected, determining a position of at least one dust pollution source based on the environmental data and the street data, and treating the dust pollution.

5 Claims, 7 Drawing Sheets

(56) References Cited

FOREIGN PATENT DOCUMENTS

| | | | |
|---|---|---|---|
| CN | 109932988 A | | 6/2019 |
| CN | 111088768 A | | 5/2020 |
| CN | 111832814 | * | 10/2020 |
| CN | 112242050 A | | 1/2021 |
| CN | 112561191 A | | 3/2021 |
| CN | 113506049 A | | 10/2021 |
| KR | 20200106266 A | | 9/2020 |
| WO | 2021118819 A1 | | 6/2021 |

OTHER PUBLICATIONS

Shao, Zehua, Exploration and Research on the Structure of Internet of Things, Internet of Things Technologies Reliable Transmission, 2015, 10 pages.

Shao, Zehua, The Internet of Things sense the world beyond the world, China Renmin University Press, 2017, 30 pages.

Shao, Zehua, Smart City Architecture, Internet of Things Technologies Intelligent Processing and Application, 2016, 7 pages.

White Paper on Urban Brain Development, Smart City Standard Working Group of National Beacon Commission, 2022, 59 pages.

First Office Action in Chinese Application No. 202210352984.4 dated May 12, 2022, 22 pages.

Zhu, Yunan, Research on Analysis and Prediction of Urban Air Pollution Network based on Intensive Data, Chinese Doctoral Dissertations & Master's Theses Full-text Database (Master) Science Engineering I, 2021, 67 pages.

Baihaqi Siregar et al., Integrated Pollution Monitoring System for Smart City, 2016 International Conference on ICT For Smart Society, 49-52, 2016.

* cited by examiner

METHOD AND INTERNET OF THINGS (IOT) SYSTEM FOR MANAGING DUST POLLUTION IN SMART CITY

CROSS-REFERENCE TO RELATED APPLICATION

This application claims priority of Chinese Patent Application No. 202210352984.4, filed on Apr. 6, 2022, the contents of which are entirely incorporated herein by reference.

TECHNICAL FIELD

The present disclosure relates to the field of Internet of Things (IoT) and cloud platforms, and in particular, to a method and an IoT system for managing dust pollution in a smart city.

BACKGROUND

As the traditional method of managing environmental pollution may not achieve early detection and early treatment, so that when pollution is detected, great impact may already be caused on a large range. For dust pollution management, as the range of the impact of dust may be large, it may be more difficult to determine the position of a dust pollution source.

Therefore, it is desirable to provide methods and the IoT systems for dust pollution management in a smart city to perform an all-round detection to the city. With the IoT and a cloud platform, the dust pollution of the city may be better managed and the position of the dust pollution source may be accurately calculated when the dust pollution occurs.

SUMMARY

One or more embodiments of the present disclosure may provide for managing dust pollution in a smart city. The method may be executed by a management platform, including: obtaining one or more environmental data of an area to be detected through a sensing network platform, and one or more street data associated with the environmental data, the environmental data may at least include dust data indicating dust information in the air; determining whether there is dust pollution in the area to be detected based on the environmental data; in response to determining that there is dust pollution in the area to be detected, determining a position of at least one dust pollution source based on the environmental data and the street data and treating the dust pollution.

One or more embodiments of the present disclosure provide an IoT system for managing dust pollution in a smart city, including a user platform, a service platform, a management platform, a sensing network platform, and an object platform. The user platform may be configured to obtain user's needs; the service platform may be configured to obtain user's needs from the user platform, and provide services to the user based on the user's needs; the management platform may be configured to obtain one or more environmental data of the area to be detected through the sensing network platform, and obtain one or more street data associated with the environmental data; the environmental data may at least include dust data indicating dust information in the air; determine whether there is dust pollution in the area to be detected based on the environmental data; in response to the determining that there is dust pollution in the area to be detected, determine a position of at least one dust pollution source and treat the dust pollution based on the environmental data and the street data; the sensing network platform may be configured to obtain initial environmental data and initial street data from the object platform, and generate environmental data and street data based on the initial environmental data and the initial street data; the object platform may be configured to obtain the initial environmental data and the initial street data.

One or more embodiments of the present disclosure provide a computer-readable storage medium storing computer instructions, wherein when reading the computer instructions in the storage medium, a computer implements the method for managing dust pollution in a smart city.

BRIEF DESCRIPTION OF THE DRAWINGS

The present disclosure will be further described in the way of exemplary embodiments, which will be described in detail by the drawings. These embodiments are not limited, in these embodiments, the same number denote the same structure, where.

DETAILED DESCRIPTION

Figure 1:
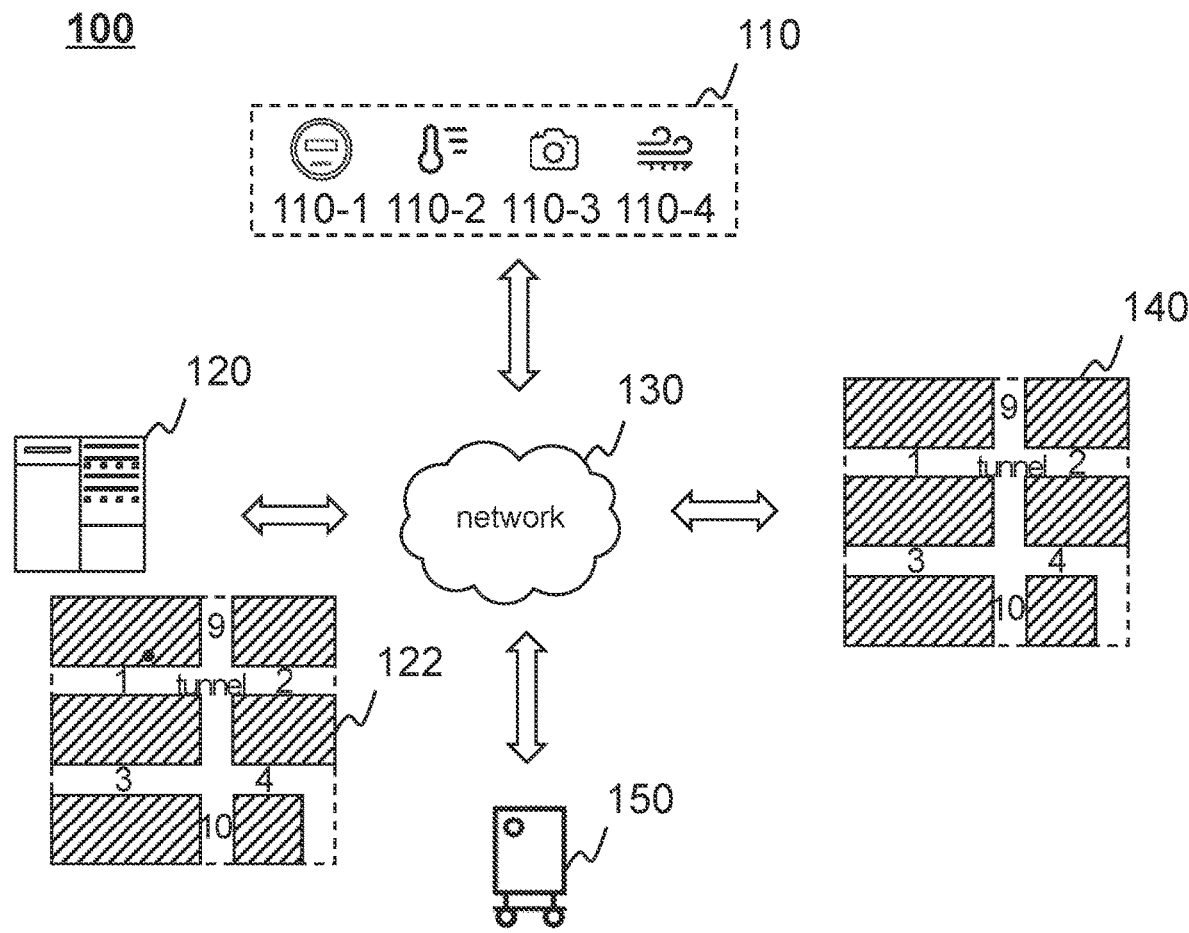
FIG. 1 is a schematic diagram illustrating an application scenario of an IoT system for managing dust pollution in a smart city according to some embodiments of the present disclosure.

The technical solution of the present disclosure embodiment is more clearly described below, and the accompanying drawings need to be used in the description of the embodiments will be briefly described below. It will be apparent that the drawings in the following description are merely some examples or embodiments of the present disclosure, and those of ordinary skill in the art will apply the disclosure to these drawings without the premise of creative labor in other similar scenes. Unless obviously obtained from the context or the context illustrates otherwise, the same numeral in the drawings refers to the same structure or operation.

It should be understood that "systems", "devices", "unit", and/or "modules" used herein are a method for distinguishing different components, elements, components, partial or assemblies of different levels. However, if other words may be achieved, the words may be replaced by other expressions.

As shown in the present disclosure and the claims, unless the context clearly prompts the exception, "a", "one", and/or "the" is not a disclosure, and the number may be included. In general, the term "comprising" and "comprising" only prompts steps and elements that include explicitly identified, and these steps and elements do not constitute a row of rows, methods or devices that may also contain other steps or elements.

The flowchart is used in this disclosure to illustrate the operations performed by the system in accordance with an embodiment of the present disclosure. It should be understood that the front or rear operation is not necessarily performed in order to accurately. Instead, each step may be processed in reverse or simultaneously. At the same time, other operations may also be added to these processes or to remove one step or step operation from these processes.

As people pay more and more attention to the environment, the standard of environmental management is further improved, which requires environmental management personnel to prevent the spread of pollution sources, and minimize the impact of pollution sources on environments in wide ranges.

In view of this, the present disclosure provides a method and IoT system for managing dust pollution in a smart city. Through the system, the environment of the city may be comprehensively monitored, and the environmental situation of the city may be obtained at any time to make judgements. When there is pollution in the city, the pollution source may be treated in time, so that pollution problems may be solved on the source to prevent further spreading of the pollution.

FIG. 1 is a schematic diagram illustrating an application scenario of an IoT system for managing dust pollution in a smart city according to some embodiments of the present disclosure.

As shown in FIG. 1, the application scenario of the IoT system for managing dust pollution in a smart city includes an environmental data obtaining device 110, a management platform 120, a network 130, street data 140, and a sweeping terminal 150.

In some embodiments, IoT system for managing dust pollution in a smart city 100 may be configured to monitor the environment of the city to determine a position of a pollution source. For example, the system may be configured to monitor a dust situation of the city, and determine whether there is dust pollution in the city based on the dust situation. In response to the determining that there is dust pollution, the position of the dust pollution source may be determined.

In some embodiments, IoT system for managing dust pollution in a smart city 100 may further process pollutants based on a pollution condition in the city. For example, the system may sweep the dust.

In some embodiments, the IoT system for managing dust pollution in a smart city may further be applied to manage other types of pollutions, including but not limited to water pollution, air pollution, land pollution, or the like.

The environmental data obtaining device 110 may be configured to obtain environmental data. More information on environmental data may refer to FIG. 2 and related descriptions, which will not be repeated here. The environmental data obtaining device may include, but not limited to, an air detection terminal 110-1, a water quality detection terminal 110-2, an image obtaining device 110-3, and a wind direction data obtaining device 110-4, etc. The IoT system for managing dust pollution in a smart city may further include an object platform. The environmental data obtaining device 110 may be configured in the object platform. The object platform may obtain initial environmental data by the environmental data obtaining device 110, and transmit the initial environmental data to a sensing network platform for processing to obtain the environmental data. More information on the object platform and the sensing network platform may refer to FIG. 2, FIG. 6 and related descriptions, which will not be repeated here. In some embodiments, the environmental data obtaining device 110 may be configured on each road to obtain environmental data on the road. For example, an air detecting device may be preinstalled on each street and perform direct sampling to the air of the streets, analyze air component data, and transmit detection data to a management platform 120. For example, a water quality detection terminal may be preinstalled in each sewer to detect the components of the water body flowing by it, and transmit the detection data to the management platform 120.

The management platform 120 may be configured to process data and/or information from at least one component or external data source (e.g., cloud data center) from the application scenario 100. The management platform 120 is configured with one or more processing devices for processing data and/or scenes. For example, the management platform 120 may obtain environmental data obtained by the environmental data obtaining device, and determine the positions 122 of one or more dust pollution sources based on the obtained environmental data and street data. For another example, the management platform 120 may allocate the sweeping terminal 150 to sweep the dust.

The network 130 may include any suitable network capable of facilitating information and/or data exchange of the application scenario 100. In some embodiments, information and/or data may be exchanged through network 130 between one or more components of the application scenario 100. For example, the management platform 120 may obtain the environmental data and the street data 140 over network 130. For another example, the management platform 120 may send an instruction of sweeping the pollutants through the network 130 to a sweeping vehicle terminal. In some embodiments, one or more components of the scenario 100 may be connected to an external data source through the network 130. For example, the management platform 120 may send air quality of city streets, work plans of street dust-cleaning, etc. to the user terminal.

A street data obtaining device may obtain the street data 140. More information on the street data 140 may refer to FIG. 2 and related descriptions, which will not be repeated here. In some embodiments, the street data obtaining device can be set in the object platform. The street data obtaining device may be configured in the object platform. The street data obtaining device may include a camera. The object platform may take images of the street captured by the camera as an initial street data; and transmit the initial street data to the sensing network platform for processing to obtain the street data. More information on the street data and the initial street data may refer to FIG. 2, FIG. 6 and related descriptions, which will not be repeated here.

The cleaning terminal 150 may be a terminal that sweeps the pollutants. The cleaning terminal 150 includes, but is not limited to, a sweeping vehicle terminal for sweeping the dust, a purifying terminal for purifying the water, an air filter for filtering the harmful materials in the air, or the like. More information on the sweeping vehicle may refer to FIG. 2 and related descriptions, which will not be repeated here.

Figure 2:
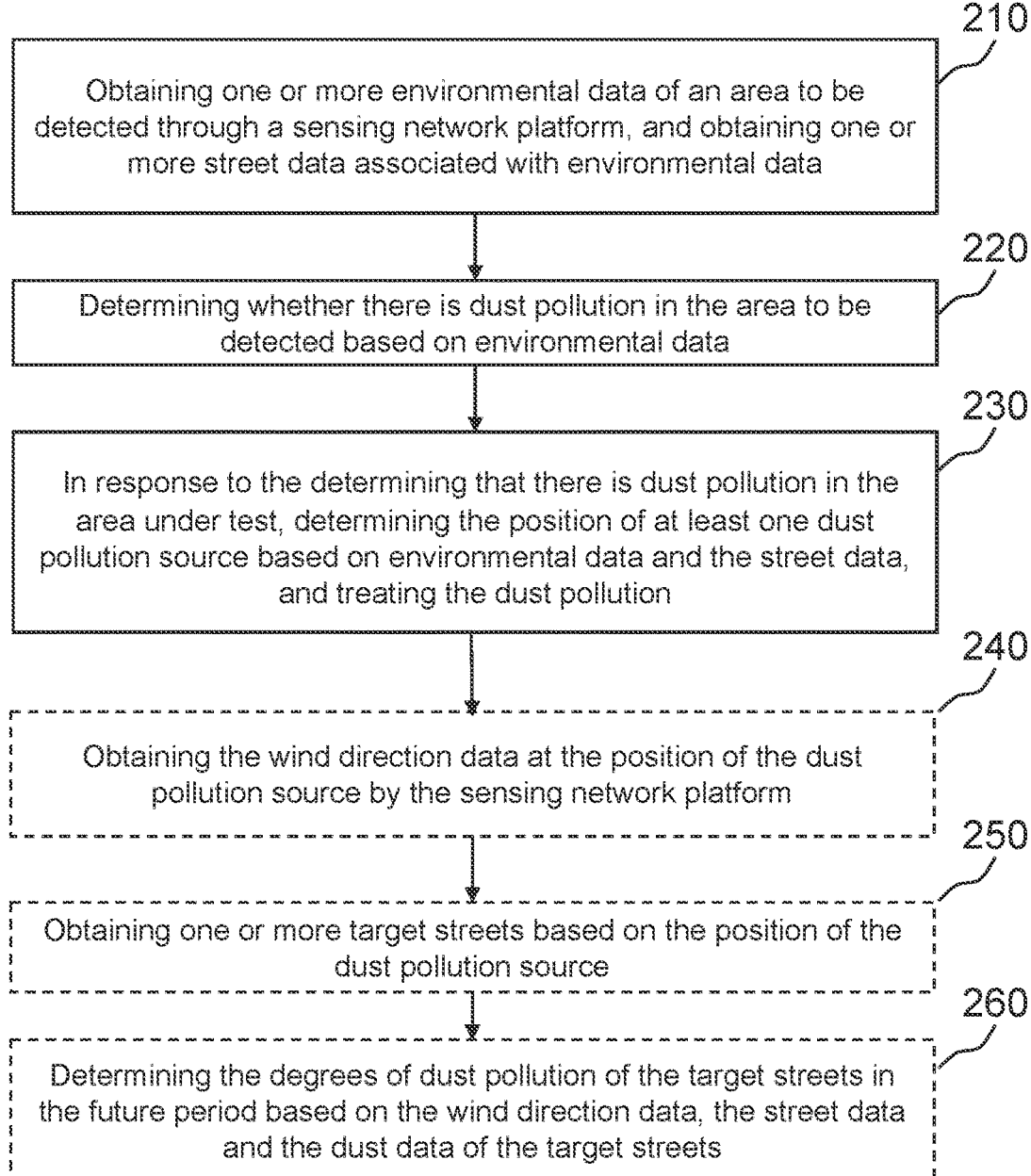
FIG. 2 is a flowchart illustrating an exemplary method for managing the dust pollution in a smart city according to some embodiments of the present disclosure.

FIG. 2 is a flow chart illustrating an exemplary method for managing the dust pollution in a smart city according to some embodiments of the present disclosure.

In some embodiments, process 200 may be executed by a management platform 630. As shown in FIG. 2, the process 200 includes one or more of the following operations.

In 210, obtaining one or more environmental data of an area to be detected through a sensing network platform, and obtaining one or more street data associated with the environmental data.

The area to be detected may be an area where dust pollution management is implemented. The range of the area to be detected may be determined according to the actual demand of dust pollution management. For example, in the situation where the management platform needs to implement dust pollution management to the whole city, the area to be detected may be the whole city. The area to be detected may further be obtained in other ways.

Environmental data may be various data related to the environment. The environmental data may at least include dust data indicating dust information in the air. The dust data may be data related to dust. For example, the dust data may include, but is not limited to, dust range, dust height, the concentration of particulate matter in the air, dust duration, visibility of a dust area, or the like. The environmental data may further include other data. For example, water data, air data, building distribution data, or the like. The water data may include river data in the area, rainfall data, air humidity, or the like.

The environmental data may be obtained by the management platform from the sensing network platform. For example, the management platform may summarize the environmental data of the sensing network platform. The management platform may further obtain environmental data in other ways, including but not limited to, obtain the data from the Internet, etc. More information on the sensing network platform may refer to FIG. 6 and related descriptions, which will not be repeated here.

In some embodiments, the environmental data may be determined by the initial environmental data obtained by the sensing network platform.

Initial environmental data may be unprocessed environment-related data obtained by the devices, for example, the electrical signals related to wind direction data obtained by a wind direction data obtaining device. The initial environmental data may at least include initial dust data, and the initial dust data may be dust data obtained by an air detection terminal.

In some embodiments, the sensing network platform may obtain the initial environmental data through the environmental data obtaining device configured in the object platform. The sensing network platform may obtain the environmental data by performing data processing on the received initial environmental data. More information on the environmental data obtaining device may refer to FIG. 1 and related descriptions, which will not be repeated here. For example, initial air data obtained from the air detection terminal by the sensing network platform may be (0.3, 1.5, 0.2). The sensing network platform may process the initial air data; and determine that the concentration of sulfur dioxide in the air is 0.3 ug/m$^3$, the concentration of nitric oxide is 1.5 ug/m$^3$, and the degree of dust pollution is 0.2 mg. For another example, the sensing network platform may obtain a live image obtained by an image obtaining device; and input the live image (e.g., environment image) to a dust data determination model; the model may output dust data in the live image. The dust data determination model may be a convolutional neural network model.

The dust data may further be obtained in other way, including, but not limited to manual input by the management personnel directly, or the like.

The street data may be various data related to streets, and the distribution of the streets may be obtained through the street data. For example, the street data may include, but not limited to, a position of a street, the relationship between streets, etc., households in a street, business information and manufacturer information in a street, or the like.

In some embodiments, when obtaining the environmental data, the management platform may first classify the environmental data according to the street data, and then respectively summarize the environmental data based on the classification. For example, the existing street data includes data of street A, street B and street C. The management platform may respectively obtain environmental data of street A, street B and street C; then respectively summarize the street data and the environmental data corresponding to the streets.

The street data may be obtained from the sensing network platform by the management platform. The management platform may obtain the street data from the sensing network platform through a variety of possible ways, including but not limited to image processing, data cleaning, or the like.

In some embodiments, the street data may be determined by initial street data obtained by the sensing network platform; and the sensing network platform may obtain the initial street data from the object platform.

The initial street data may be data related to streets obtained by a street data obtaining device. For example, the image of street 1 captured by the image obtaining device may be considered as the initial street data.

In some embodiments, the street data obtaining device may be configured on the object platform. The sensing network platform may obtain initial street data from the street data obtaining device and process the initial street data to obtain the street data. For example, the sensing network platform may use the camera to obtain the street images of the street 1, the street 2 and the street 3. The sensing network platform may extract positions of the street 1, the street 2 and the street 3 and obtain the relationship between the streets by image processing.

In some embodiments, the sensing network platform may input the obtained initial street data to a street data recognition model, and the street data recognition model may output street data. The street data recognition model may include, but is not limited to, convolutional neural network models, or the like.

In some embodiments, the street data recognition model may be obtained through training a plurality of first training samples with labels. For example, the sensing network platform may input a plurality of first training samples with labels to a preliminary street data recognition model; construct a loss function by the labels and the result of the preliminary street data recognition model; and iteratively update the parameters of the preliminary street data recognition model based on the loss function. When the loss function of the preliminary street data recognition model meets preset conditions, the model training may be completed, and the trained street data recognition model may be obtained. The preset conditions may include loss function convergence, the number of iterations reaches a threshold, or the like. The labels may be sample street data corresponding to the first training samples, and the sample street data may at least be obtained by manual labeling. Methods of training the street data recognition model include, but are not limited to, gradient descent, regularization, and conjugate gradient methods, or the like.

In 220, determining whether there is dust pollution in the area to be detected based on the environmental data.

The dust pollution may be pollution caused by dust particles. In some embodiments, the case where low visibility caused by dust in the air may be considered as dust pollution. In some embodiments, the management platform may compare the obtained dust data with a preset pollution threshold, when dust data is greater than the preset pollution threshold, that there is dust pollution may be determined. For example, the preset pollution threshold may be a concentration of particulate matter in the air greater than 0.3 mg; when the dust data indicates that the current concentration of the particulate matter in the air is greater than 0.3 mg, the management platform may determine that there is dust pollution in the area to be detected.

When the management platform determines that there is no dust pollution in the area to be detected, it may continue to obtain environmental data; and based on the newly obtained environmental data, make continuous determination on whether there is dust pollution in the area to be detected. Other operations may further be performed as well when the management platform determines that there is no dust pollution in the area to be detected.

In 230, in response to the determining that there is dust pollution in the area to be detected, determining a position of at least one dust pollution source based on the environmental data and the street data, and treating the dust pollution.

A dust pollution source may be a source that causes the dust pollution. A position of the dust pollution source may be the position of the source of the dust pollution. For example, the longitude and latitude coordinates of the dust pollution source may be extracted as the position of the dust pollution source.

In some embodiments, the management platform may obtain a plurality of images of areas with dust pollution, then respectively extract the street data and the environmental data in the plurality of images. The management platform may determine the positions of the streets and the relationships between the streets based on the street data and the environmental data. The management platform may further determine a street where the dust pollution source locates based on the relationships between the streets and the degree of dust pollution of each street, and determine the position of the dust pollution source based on the position of the street.

In some other embodiments, for the dust data obtained through an air detection terminal, the management platform may obtain a position of the corresponding air detection terminal when obtaining the dust data; determine the a street where the dust pollution locates as well as the position of the street based on the position of the air detection terminal and the degree of dust pollution detected; and determine the position of the dust pollution source based on the position of the street.

In some other embodiments, the management platform may determine a road network map of the area to be detected based on the street data.

The road network map may be a map of all streets within the area to be detected. The road network map may visually reflect the distribution of roads within the area to be detected. In some embodiments, nodes of the road network map may be streets, and a property of a node may include, but not limited to names of streets, positions of the streets, environments of the streets, or the like. Edges of the road network map may be relationships between the streets, and a property of the edges may include, but not limited to, the connections between the streets, or the like. For example, as shown in street data 140 in FIG. 1, street 1 and street 2 may be used as nodes in the map. Since street 1 and street 2 are interconnected streets, the way of their connection is straight connection; therefore, there is an edge between street 1 and street 2, which represents that they are geographically connected. The property of the edge may include straight connection.

In some embodiments, the management platform may extract data of each street from the street data, and establish a road network map based on the data of each street. For example, the management platform may obtain information including a name, a position, a length, and a connected street, a connection way, etc. of each street; use the name of the street as the node, use the position of the street, the length of the street, and other data representing the property of the street as the property of the node; and determine whether the street is connected to other streets according to the relationships between the street and the other streets, and take the connection way of the connected streets with the street as the property of the edge.

In some embodiments, the management platform may determine the position of at least one dust pollution source based on road network map and the environmental data, and treat the dust pollution.

In some embodiments, the management platform may determine streets with dust pollution and the degrees of pollution of the streets based on the environmental data; and determine the position of the at least one dust pollution source based on the relationship between the streets with dust pollution and the changes of the degree of pollution. For example, the management platform may process the environmental data, and found that there is dust pollution in street 1, street 9 and street 2; the degree of dust pollution in street 1 is 5.8 mg; the degree of dust pollution in street 9 is 3.2 mg; and the degree of dust pollution in street 2 is 2.8 mg. The road network map shows that the street 1, the street 9 and the street 2 are three interconnected streets. According to this, the management platform may determine that the position of the dust pollution source is on the street 1. In some embodiments of the present disclosure, since the management platform may transfer the street data into a road network map and the road network map may visually reflect the relationships between streets, the position of the dust pollution source can be more accurately determined.

In some embodiments, the management platform may further treat the dust pollution based on the position of the dust pollution source. For example, the management platform may first sweep dust at the position of the dust pollution source, and then sweep other streets being polluted due to the expansion of the dust.

In some embodiments, the management platform may further obtain positions of a plurality of sweeping vehicle terminals through the sensing network platform; and allocate the sweeping vehicle terminals to a target sweeping area based on the positions of the sweeping vehicle terminals and the degrees of dust pollution of target streets in a future period.

The sweeping vehicle terminal may be a terminal to sweep the environment. For example, a terminal to sweep the dust. The forms of sweeping vehicles may vary, including but not limited to vehicle-mounted vacuum cleaners, watering vehicles, etc.

In some embodiments, the object platform may further include the sweeping vehicle terminal. The object platform may transmit the position of the sweeping vehicle terminal through the sensing network platform to the management platform. The management platform may further obtain the position of the sweeping vehicle terminal in other ways.

The target sweeping area may be an area where dust pollution treatment is required. For example, a target street whose degree of dust pollution in the future period in operation 260 doesn't meet the standard may be commonly taken as the target sweeping area together. In some embodiments, the size of the target sweeping area may be determined according to the actual demand, and the area may be divided according to a fixed size, or according to the streets.

In some embodiments, the management platform may determine a number of sweeping vehicles according to the degree of dust pollution of a target sweeping area in the future period. When the number of sweeping vehicles in the target sweeping area is sufficient, the management platform may allocate sweeping vehicles according to the different degrees of dust pollution within the target sweeping area. For example, the average degree of pollution in area 1 in the future period is 2.3 mg, and the management platform may determine that the number of sweeping vehicles required in the area 1 is 4. For example, assuming that the number of sweeping vehicles in area 1 is 5, the management platform may determine that the numbers of sweeping vehicles required by the streets in area 1 include: street 1 requires 2 vehicles, street 2 and street 3 requires 1 vehicle each according to the degree of dust pollution in each street within area 1 (e.g., street 1: 3.1 mg, street2: 2.3 mg, street 3: 1.5 mg).

In some embodiments, the management platform may allocate one sweeping vehicle to sweep a plurality of streets for streets with low degrees of dust pollution.

In some embodiments, when the number of sweeping vehicles in the target sweeping area is insufficient, sweeping vehicle(s) in the adjacent area(s) may be dispatched to sweep the target sweeping area when the sweeping vehicles in the target area start to work.

In some embodiments of the present disclosure, the management platform may allocate sweeping vehicle terminals in advance based on the degrees of dust pollution in the future period and positions of the sweeping vehicle terminals, so that the target sweeping area may be swept timely, and the expansion of pollution area due to untimely sweeping may be avoided.

In some embodiments of the present disclosure, by obtaining the environmental data and the street data of the area to be detected, and based on the street data and the environmental data, the position of the dust pollution source may be determined. In this way, the accuracy of the determination of the position of the dust pollution source may be enhanced, so that reliable information may be provided for subsequent processing.

In 240, obtaining wind direction data at the position of the dust pollution source by the sensing network platform.

The wind direction data may be data related to the direction of air flow. The wind direction data may include, but not limited to, the direction of wind blowing, the wind power, the time of the wind blowing, or the like.

The wind direction data may be obtained from the sensing network platform by the management platform. The management platform may obtain the wind direction data from the sensing network platform in various ways.

In some embodiments, the wind direction data may be determined by initial wind direction data obtained by the sensing network platform. The sensing network platform obtains the initial wind direction data from the object platform. For example, the sensing network platform may obtain the wind direction data obtained by the wind direction data obtaining device.

In 250, obtaining one or more target streets based on the position of the dust pollution source.

The target streets may be streets where dust pollution may occur in the future, for example, the streets where dust pollution may occur in one hour later, or one day later.

In some embodiments, the management platform may determine the streets connected to the dust pollution source as the target streets. For example, the position of the dust pollution source may be in the street 1, the management platform may determine the street 2 and street 9 connected to the street 1 as the target streets.

In 260, determining the degrees of dust pollution of the target streets in the future period based on the wind direction data, the street data, and the dust data of the target streets.

The degree of dust pollution may be used to represent the severity of dust pollution in the air. In some embodiments, the management platform may determine the degree of dust pollution based on the concentration of the particulate matter in the air. For example, the management platform may determine the degree of dust pollution whose concentration of particulate matter per cubic meter of air is between 0.1 mg and 0.2 mg as light pollution; the degree of dust pollution whose concentration of particulate matter per cubic meter of air is between 0.2 mg to 0.3 mg as medium pollution; and the degree of dust pollution whose concentration of particulate matter per cubic meter of air is greater than 0.3 mg as severe pollution.

The degree of dust pollution in the future period may be the severity degree of dust pollution in the air in the future.

In some embodiments, the management platform may determine the diffusion direction and diffusion speed of the dust at the position of dust pollution source based on the wind direction data; determine the street(s) that may be affected by the diffused dust based on the diffusion direction and diffusion speed of the dust; and calculate the degree of diffuse dust pollution diffused in each target street. The management platform may further determine the degree of future dust pollution at the target street in the future period based on the wind direction data; and determine the degree of dust pollution in the future period based on the degree of future dust pollution and the degree of diffuse dust pollution of the target street.

In some embodiments, the management platform may input the wind direction data, the dust data, the position of the dust pollution source, the distance between the dust pollution source and each target street, and weather data to a pollution degree prediction model, the model may output the degree of dust pollution of each target street in the future period.

In some embodiments, the pollution degree prediction model may be obtained by training a plurality of third training samples with labels. For example, a plurality of third training samples with labels may be input to an initial pollution degree prediction model; a loss function may be constructed through the labels and the results of the initial pollution degree prediction model; and parameters of the initial pollution degree prediction model may be iteratively updated based on the loss function. When the loss function of the initial pollution degree prediction model meets the preset conditions, the model training is completed, and the trained pollution degree prediction model may be obtained. The preset conditions may include loss function convergence, the number of iterations reaches a threshold, or the like. Methods of training the pollution degree prediction model include, but are not limited to, gradient descent, regularization, and conjugate gradient methods, or the like. In some embodiments, the third training samples and the labels may be obtained by extracting historical data.

In some embodiments of the present disclosure, through predicting the degree of dust pollution of each target street in the future period, the changes of dust pollution over time may be obtained, which makes it easy to implement targeted sweeping strategies according to the changes of dust pollution.

Figure 3:
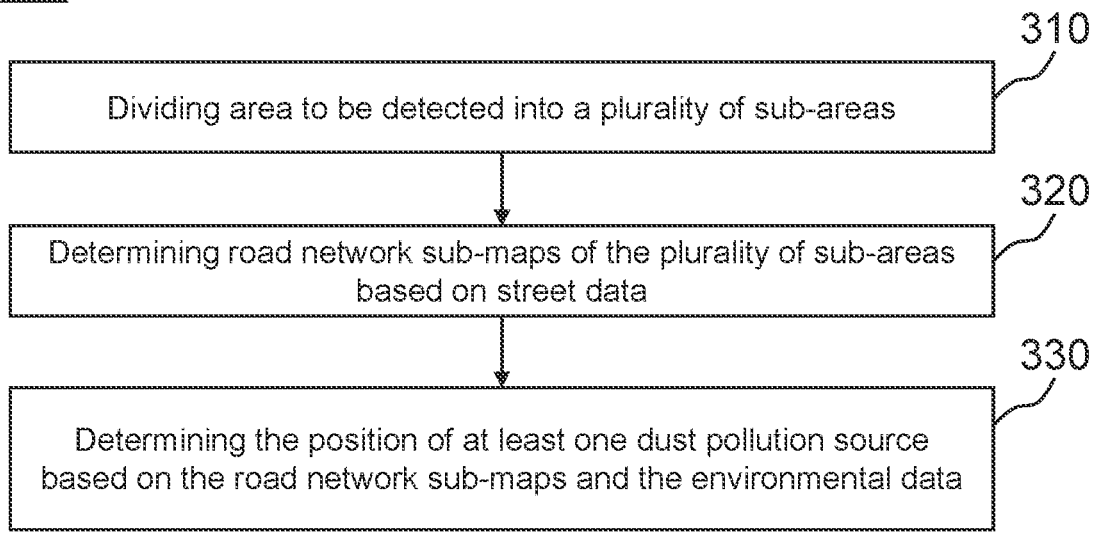
FIG. 3 is an exemplary flowchart illustrating a process of the determination of position of dust pollution source according to some embodiments of the present disclosure.

FIG. 3 is an exemplary flowchart illustrating a process of the determination of position of dust pollution source according to some embodiments of the present disclosure. In some embodiments, process 300 may be performed by a management platform 630. As shown in FIG. 3, the process 300 includes the following operations.

In 310, dividing an area to be detected into a plurality of sub-areas.

The sub-areas may be areas obtained by dividing the area to be detected. The management platform may divide the area to be detected in varies ways to obtain a plurality of sub-areas.

In 320, determining road network sub-maps of the plurality of sub-areas based on street data.

A road network sub-map of a sub-area may be a map constructed by all streets in the sub-area. The road network sub-map may intuitively reflect the distribution of streets/roads within the sub-area. The nodes, edges, properties of nodes and properties of the edges of the road network sub-map may be similar to those in the road network map in FIG. 2. More information on the road network sub-map may refer to FIG. 2 and related descriptions, which will not be repeated here.

In some embodiments, the management platform may include a plurality of management sub-platforms. Each management sub-platform may determine a road network sub-map of a sub-area based on the street data of each sub-area. For example, the management platform may include a management information-integrated management platform. The management information-integrated management platform may distribute sub-areas that need to be processed to the management sub-platforms. A management sub-platform may obtain street data from the sensing network platform according to the sub-area processed itself; extract data related to the streets (street data) in the sub-area from the street data; and establish a road network sub-map of the sub-area based on the extracted street data.

In 330, determining the position of at least one dust pollution source based on the road network sub-maps and the environmental data.

In some embodiments, the management platform may determine the position of the dust pollution source based on the road network sub-maps and the environmental data respectively. For example, the management platform may respectively process the road network sub-maps and the environmental data of sub-area 1, sub-area 2 and sub-area 3 through management sub-platform 1, management sub-platform 2, and management sub-platform 3. The management information-integrated management platform may determine the streets where the dust pollution sources locate in the area based on the processing results of the sub-areas 1, 2, 3 transmitted by the management sub-platforms 1, 2, and 3.

In some embodiments of the present disclosure, the positions of the dust pollution sources in each sub-area may be determined by dividing the area to be detected into a plurality of sub-areas, thereby enhancing the processing efficiency, and making the load capacity of the management platform higher.

It should be noted that the description of method for managing dust pollution in a smart city is merely for example and description, without limiting the scope of application of the present disclosure. For those skilled in the art, various modifications and changes can be made to the process of smart urban dust pollution management methods under the guidance of the present disclosure. However, these corrections and changes are still within the scope of the present disclosure.

Figure 4:
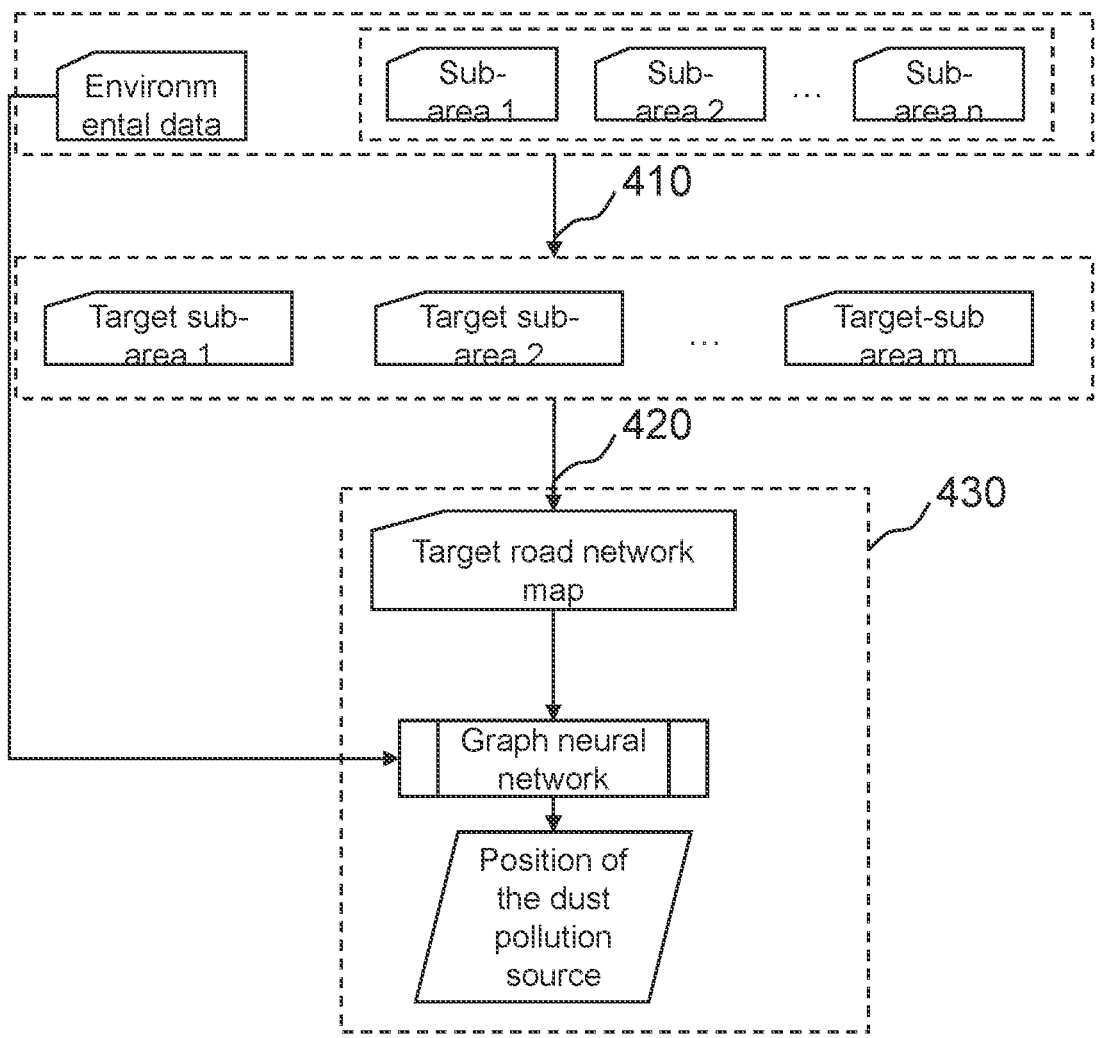
FIG. 4 is a schematic diagram illustrating a process of the determination of the position of the dust pollution source according to some embodiments of the present disclosure.

FIG. 4 is a schematic diagram illustrating a process of the determination of the position of the dust pollution source according to some embodiments of the present disclosure. In some embodiments, the content shown in schematic diagram 400 may be executed by the management platform 630. As shown in FIG. 4, the schematic diagram 400 may include the following contents.

In 410, determining one or more target sub-areas with dust pollution from a plurality of sub-areas based on environmental data.

The target sub-area may be a sub-area with dust pollution. For example, an area where the degree of dust pollution is greater than 0.3 mg may be determined as the target sub-area.

In some embodiments, the management platform may process dust data in the environmental data; and determine one or more target sub-areas whose degree of dust pollution does not meet the preset pollution threshold based on the dust data and the preset pollution threshold. More information on the preset pollution threshold may refer to FIG. 2 and related descriptions, which will not be repeated here. For example, the preset pollution threshold is 0.3 mg, and the management platform may determine m sub-areas whose degree of dust pollution is greater than 0.3 mg from n sub-areas as the target sub-areas.

In 420, determining a target road network map based on the road network sub-maps of the target sub-areas; wherein the target road network map may at least include the streets of the target sub-areas and the relationships between the streets.

The target road network map may be a map of all streets in the target sub-areas. The target road network map may at least include the streets and the relationship between the streets of the target sub-areas. The target road network map may intuitively reflect the distribution of streets in areas with dust pollution. Nodes of the target road network map may be streets, and properties of the node may include, but not limited to the names, positions or environments of the streets, or the like; and the edges of the target road network map may be the relationships between the streets, and the properties of the edges may include, but not limited to, the connection relations between the streets, or the like. For example, the street data 140 in FIG. 1 may be considered as a target sub-area constructed by street 1, street 2, street 3, street 4, street 9 and street 10. The street 1, street 2, street 3, street 4, street 9 and street 10 in the map may be taken as the nodes in the target road network map. Since street 1 and street 2 are interconnected streets, the way of their connection is straight connection; therefore, there is an edge between street 1 and street 2, which represents that they are geographically connected. The data of the edge may include straight connection.

In 430, obtaining the position of at least one dust pollution source based on the target road network map and the environmental data, by a graph neural network.

In some embodiments, the management platform may input the target road network map and the environmental data into the graph neural network, and the graph neural network may output a position of the at least one dust pollution source.

In some embodiments, the graph neural network may be obtained based on the supervised training of initial graph neural network by second training samples; and the second training samples may include a plurality of training sample sets. Each training sample set may include sample target road network maps and sample environmental data; and the street where the sample dust pollution source locates may be taken as a label. The street where the sample dust pollution source locates may at least be obtained by manual labeling. For example, the management platform may input a plurality of second training samples with labels to the initial graph neural network; construct a loss function by the labels and the result of the initial graph neural network; and iteratively update parameters of the initial graph neural network based on the loss function. When the loss function of the initial graph neural network meets preset conditions, the model training is completed, and a trained graph neural network model may be obtained. The preset conditions may include loss function convergence, the number of iterations reaches a threshold, or the like. Methods of training graph neural network models include, but not limited to, gradient descent, regularization, and conjugate gradient methods, or the like.

Figure 5:
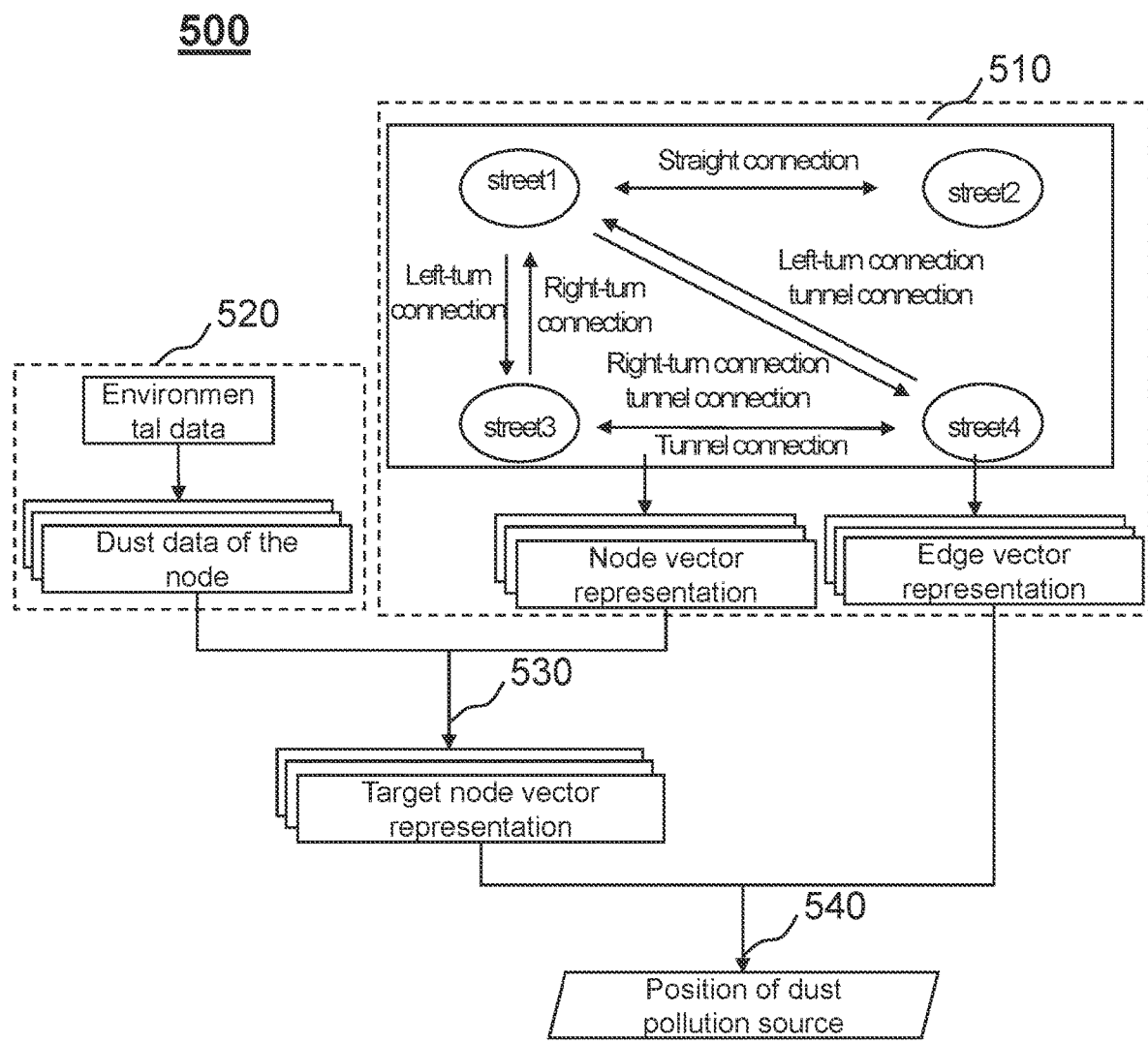
FIG. 5 is an exemplary schematic diagram illustrating a process of the determination of position of a dust pollution source according to some embodiments of the present disclosure.

More information on determining the position of dust pollution source with graph neural network may refer to FIG. 5 and related descriptions, which will not be repeated here.

In some embodiments of the present disclosure, the management platform may extract the road network sub-maps of the sub-areas with dust pollution to form the target road network map, so that only sub-areas with dust pollution may be processed, which reduces the pressure of processing and enhances the processing efficiency.

FIG. 5 is an exemplary schematic diagram illustrating a process of the determination of position of a dust pollution source according to some embodiments of the present disclosure. In some embodiments, the content shown in schematic diagram 500 may be executed by the management platform 630. As shown in FIG. 5, the schematic diagram 500 may include the following contents.

In 510, extracting a node vector representation of each node and an edge vector representation of each edge in a target road network map.

The node may be a street, and the node vector representation at least includes the name, position and direction of the street, or the like. For example, for the node representing street 1, the node vector representation may be (Road I, A, east-west direction, 100), indicating that the name of the street 1 is Road I, the position of the street is A, and the street 1 is located along an east-west direction with 100 meters long.

An edge is the relationship between the streets, and the edge vector representation includes at least the relationship between the streets. For example, the relationship between the street 1 and the street 2 is straight connection, then the edge vector representation between the street 1 and the street 2 may be (straight connection, straight connection). For another example, the relationship between the street 1 and the street 3 includes (left-turn connection, tunnel connection) and (right-turn connection, tunnel connection), then the edge vector representation of the street 1 and the street 3 may be (left-turn connection, tunnel connection, right-turn connection, tunnel connection).

In some embodiments, the graph neural network may perform image recognition on the input target road network map; extract the nodes, properties of nodes, edges, and properties of edges; form the node vector representations based on the properties of the extracted nodes; and form the edge vector representations based on the properties of the edges.

In 520, extracting dust data of each node based on environmental data.

In some embodiments, the graph neural network may extract dust data of each node from the environmental data. For example, the graph neural network may extract the dust data of the street with the same name from the environmental data according to the name of node 1 of Road I.

In 530, adding the dust data to the node vector representation of the node to obtain a target node vector representation.

The target node vector representation may be a vector representation obtained after adding the dust data to the node vector representation. For example, the dust data of the node of street 1 is 3.8 mg, and the target node vector representation of the street 1 may be (Road I, A, east-west direction, 100, 3.8).

The graph neural network may add the dust data to the corresponding node vector representation by various feasible ways, including but not limited to, adding directly, adding dust data after processing, or the like.

In 540, determining the position of the at least one dust pollution source based on the target node vector representation and the edge vector representation.

In some embodiments, the graph neural network may determine whether a street is the position of the dust pollution source based on features of the target node vector representation and the edge vector representation. The graph neural network may determine the position of dust pollution source by various feasible ways, including, but not limited to linear regression, logistic regression, random forest, or the like.

In some embodiments of the present disclosure, by inputting a plurality of influencing factors as vectors to the graph neural network, the graph neural network may better recognize the position of the dust pollution source, which may improve the accuracy of the determined position of the dust pollution source.

Figure 6:
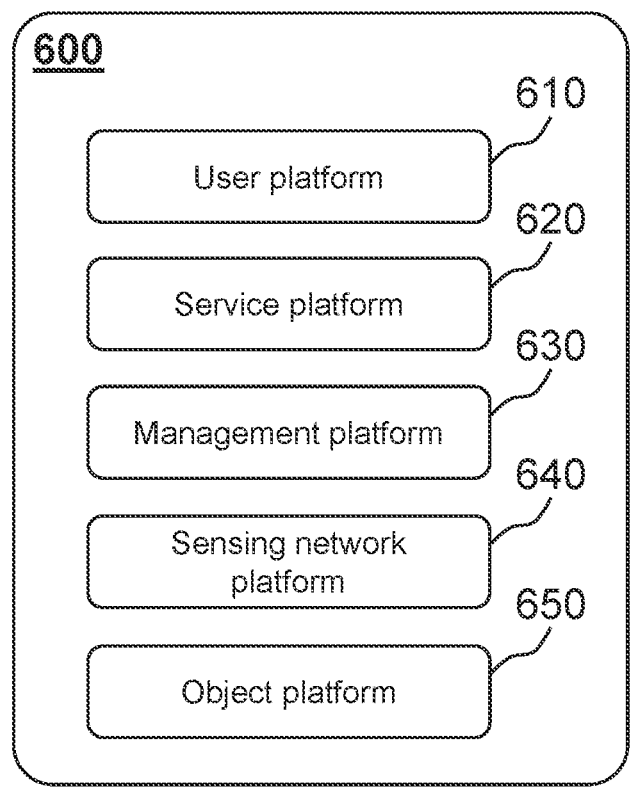
FIG. 6 is a schematic diagram illustrating the IoT system for managing dust pollution in a smart city according to some embodiments of the present disclosure.

FIG. 6 is a schematic diagram illustrating the IoT system for managing dust pollution in a smart city according to some embodiments of the present disclosure. In some embodiments, the IoT system 600 for managing dust pollution in a smart city may include a user platform 610, a service platform 620, a management platform 630, a sensing network platform 640, and an object platform 650.

The user platform 610 may be configured to obtain user's needs. The user's needs may be the services provided by the system under the requirements of the user. In some embodiments, the user may obtain information related to urban dust pollution management through the user platform. For example, the citizens may obtain information about the air quality of urban streets, plans of the street dust-cleaning work, or the like. In some embodiments, a user may send a demand instruction to IoT system for managing dust pollution in a smart city through the user platform. For example, the citizens may report to the system that the dust pollution exists in a certain area, and require the system to process the pollution.

The service platform 620 may be configured to obtain user's needs from the user platform, and provide services for users based on the user's needs. For example, the service platform may display current air quality of the city and the plans of the street dust-cleaning work to the user. For another example, the service platform may feedback the processing results according to the user's reports.

In some embodiments, the service platform 620 may include a plurality of service sub-platforms for processing data, a service platform database for transmitting data, and a service information-integrated management platform. The service information-integrated management platform may obtain user's needs from the user platform. The service platform database may store and/or receive user's needs and transmit them to the service sub-platform. The service sub-platform may process the user's needs, and provide feedback information for the user according to his/her needs.

In some embodiments, the service platform 620 may further send instructions to the management platform based on the user's needs, and feedback the execution result of the management platform to the user. For example, the service platform may instruct the management platform to determine whether there is dust pollution in area A according to dust pollution information in area A reported by a user. In response to the determining that there is dust pollution in area A, sweeping may be performed to the dust pollution. When the sweeping is completed, the service platform may send the processing result to the user through the user platform.

The management platform 630 may be configured to obtain one or more environmental data of the area to be detected through the sensing network platform, and obtain one or more street data associated with the environmental data; the environmental data may at least include dust data indicating dust information in the air; determine whether there is dust pollution in the area to be detected based on environmental data; in response to the determining that there is dust pollution in the area to be detected, determine the position of at least one dust pollution source based on the environmental data and the street data, and treat the dust pollution. More information on the area to be detected, the environmental data, the street data, the dust data, and the determination of the dust pollution and the position of the dust pollution source may refer to FIG. 2 and related descriptions, which will not be repeated here.

In some embodiments, the management platform 630 may further be configured to obtain wind direction data at the position of the dust pollution source through the sensing network platform; determine one or more target streets based on the position of the dust pollution source; and determine the degrees of dust pollution of the target streets in the future period based on the wind direction data, the street data, and the dust data of the target streets. More information on the wind direction data, the target street and its degree of dust pollution and related descriptions may refer to FIG. 2 and related descriptions, which will not be repeated here.

In some embodiments, the management platform 630 may further be configured to obtain positions of a plurality of sweeping vehicle terminals through the sensing network platform; and allocate target sweeping areas for the sweeping vehicle terminals based on the positions of the sweeping vehicle terminals and the degrees of dust pollution of the target streets in the future period.

The sensing network platform 640 may be configured to obtain initial environmental data and initial street data from the object platform, and generate the environmental data and the street data based on the initial environmental data and the initial street data.

In some embodiments, the sensing network platform 640 may include a plurality of sensing sub-platforms, a sensing network platform database, and a sensing information-integrated management platform. The sensing sub-platforms may be configured to process data. The sensing network platform database may be configured to transmit data. The management information-integrated management platform may be configured to manage data. The sensing network platform database may be configured to obtain the initial environmental data and the initial street data from the object platform. The plurality of sensing sub-platforms may be configured to obtain the initial environmental data and the initial street data from the sensing network platform database; and process the initial environmental data and the initial street data to obtain the environmental data and the street data. The sensing network platform database may further be configured to transmit the environmental data and the street data of the plurality of sensing sub-platforms to the management platform. The sensing information-integrated management platform may be configured to obtain the environmental data and the street data from the plurality of sensing sub-platforms through the sensing network platform database; and transmit the environmental data and the street data to the management platform. More information on the initial environmental data, the initial street data, the environmental data, and the street data may refer to FIG. 2 and related descriptions, which will not be repeated here.

In some embodiments, the sensing network platform 640 may further obtain the wind direction data and transfer the wind direction data to the management platform.

In some embodiments, the sensing network platform 640 may further obtain the positions of the sweeping vehicle terminals and transmit the positions of the sweeping vehicle terminals to the management platform.

In some embodiments of the present disclosure, the sensing network platform may obtain the initial environmental data and the initial street data through the plurality of sensing sub-platforms; and process the obtained data, which may improve the efficiency of data processing.

The object platform 650 may be configured to obtain the initial environmental data and the initial street data. The object platform 650 may include a plurality of environmental data obtaining devices and street data obtaining devices. For example, the object platform 650 may include an air data detection terminal, a water quality detection terminal, an image obtaining device, or the like. More information on the initial environmental data and the initial street data may refer to FIG. 2 and related descriptions, which will not be repeated here.

In some embodiments, the object platform 650 may further include a wind direction data obtaining device. The object platform may send the data related to the wind direction obtained by the wind direction data obtaining device to the management platform through the sensing network platform.

In some embodiments, the object platform 650 may further include a sweeping vehicle terminal. The object platform may transmit data related to the position of sweeping vehicle terminal through the sensing network platform to the management platform.

It should be noted that the above descriptions of the IoT system for managing dust pollution in a smart city and its modules are only for the purpose of illustration, and cannot limit the scope of the disclosure. It will be appreciated that for those skilled in the art, after understanding the principle of the system, the individual modules may be arbitrarily combined without departing from this principle, or the subsystem is connected to other modules. In some embodiments, the user platform 610, the service platform 620, the management platform 630, the sensing network platform 640, and the object platform 650 may be different modules in a system, or one module to implement the functions of the above two or more modules. For example, each module can share a storage module, and each module can also have respective storage modules. Such type of deformation is within the scope of the disclosure.

Figure 7:
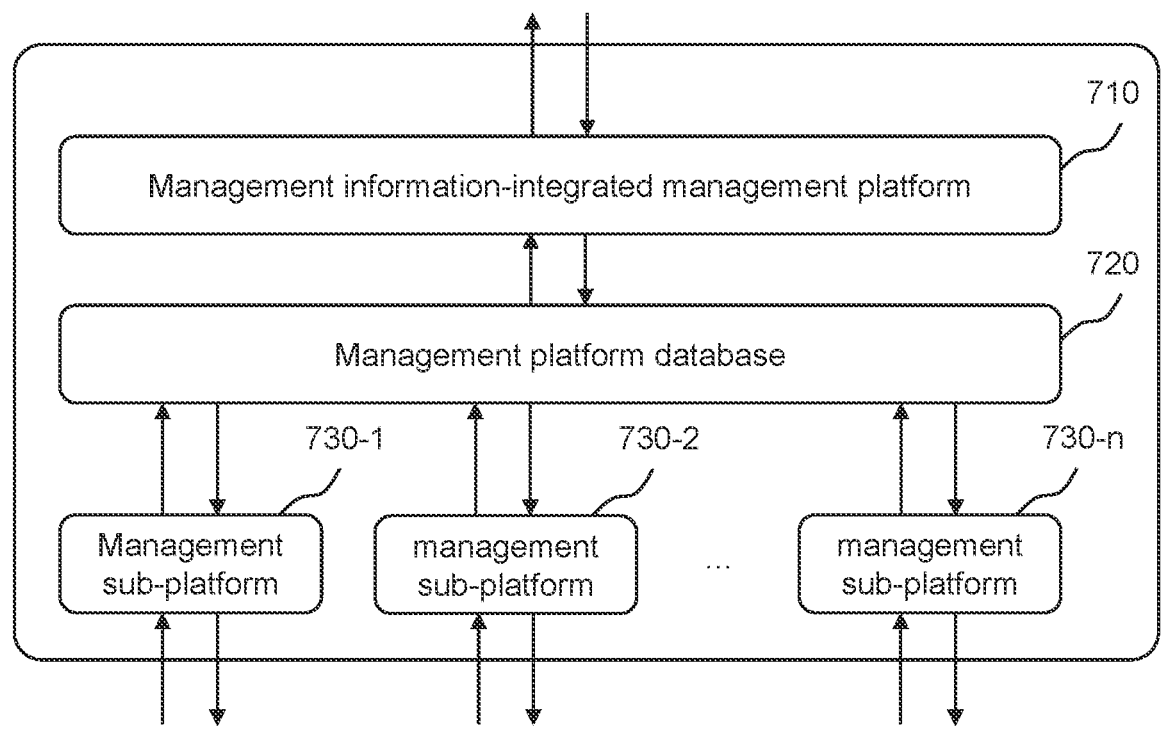
FIG. 7 is a module diagram illustrating a management platform according to some embodiments of the present disclosure.

FIG. 7 is a module diagram illustrating a management platform according to some embodiments of the present disclosure. As shown in FIG. 7, the management platform 630 may include a management information-integrated management platform 710, a management platform database 720, and a plurality of management sub-platforms 730-1, 730-1, . . . , and 730-n.

The management platform may further be configured to divide the area to be detected into a plurality of sub-areas. More information on the sub-areas and the division of the sub-areas may refer to FIG. 4 and related descriptions, which will not be repeated here.

The management information-integrated management platform 710 may be configured to obtain road network sub-maps from the management platform database; and determine the position of the at least one dust pollution source based on the road network sub-maps and environmental data. More information on the road network sub-map, the environmental data, and the determination of the position of the dust pollution may refer to FIG. 4 and related descriptions, which will not be repeated here.

The management platform database 720 may be configured to obtain road network sub-maps from the plurality of management sub-platforms. More information on the road network sub-map may refer to FIG. 4 and related descriptions, which will not be repeated here.

The plurality of management sub-platforms may be configured to determine the road network sub-maps of a plurality of sub-areas based on street data; a road network sub-map at least includes the streets of a corresponding sub-area and the relationship between the streets. More information on the road network sub-map and the determination of road network sub-map may refer to FIG. 4 and related descriptions, which will not be repeated here.

In some embodiments of the present disclosure, the management platform may obtain the road network sub-map by dividing the area to be detected into a plurality of sub-areas and respectively processing the data of each sub-area based on the plurality of management sub-platforms, which enhanced the processing efficiency.

In some embodiments, one or more embodiments of the present disclosure may further provide a computer readable storage medium. The storage medium stores computer instructions. When the computer reads the computer instructions in the storage medium, the computer performs method for managing dust pollution in a smart city.

The basic concepts have been described above, apparently, in detail, as will be described above, and does not constitute a limitations of the disclosure. Although there is no clear explanation here, those skilled in the art may make various modifications, improvements, and corrections for the present disclosure. This type of modification, improvement, and corrections are recommended in the present disclosure, so this class is modified, improved, and the amendment remains in the spirit and scope of the exemplary embodiment of the present disclosure.

Meanwhile, the present disclosure uses specific words to describe embodiments of the present disclosure. As "one embodiment", "an embodiment", and/or "some embodiments" means a certain feature, structure, or feature of the present disclosure at least one embodiment. Therefore, it should be emphasized and noted that "an embodiment" or "one embodiment" or "an alternative embodiment" or "an alternative embodiment" or "an alternative embodiment" mentioned in the present disclosure is not necessarily the same embodiment. Further, certain features, structures, or features of one or more embodiments of the present disclosure can be combined.

Moreover, unless the claims are clearly stated, the sequence of the present disclosure, the use of the digital letters, or the use of other names, is not used to define the order of the present disclosure processes and methods. Although some examples of the invention currently considered useful in the above disclosure are discussed, it is understood that such detailed purposes only, the appended claims are not limited to disclosed embodiments, but opposite, the claims are designed to cover all amendments and equivalents in accordance with the substance and range of the present disclosure. For example, although the implementation of various components described above may be embodied in a hardware device, it may also be implemented as a software only solution, e.g., an installation on an existing server or mobile device.

Similarly, it should be noted that in order to simplify the expression disclosed in the present disclosure, it is intended to help the embodiments of one or more inventive embodiments, and a plurality of features may be returned to one embodiment in the description of the present disclosure. However, this disclosure method does not mean that the features needed in the spectrum ratio of the present disclosure ratio are more characteristic. Rather, claimed subject matter may lie in less than all features of a single foregoing disclosed embodiment.

In some embodiments, a number of descriptions, attributes, should be understood, such for the numbers described in the embodiments, in some examples, "approximately", "approximation" or "generally" in some examples. Modified. Unless otherwise stated, "approximately", "approximate" or "substantially" indicates that the number is allowed to have a change in ±20%. Accordingly, in some embodiments, the numerical parameters used in the disclosure and claims are approximate, and the approximation can change according to the characteristics required by the individual embodiments. In some embodiments, numerical parameters should take into account the predetermined effective digits and the general bits reserved. Although some embodiments of the present disclosure are used to confirm the range of ranges, the range of ranges of the wide range is an approximate value, in the specific embodiment, the setting of such values is as accurate as possible within the feasible range.

For each patent, patent application, patent application publications and other materials referenced in the present disclosure, such as articles, books, instructions, publications, documents, etc., here, all of them will be incorporated herein by reference. Except for the application history documentation of the present disclosure or the conflict, there is also an except for documents (current or after the present disclosure), which are available in the present disclosure. It should be noted that any inconsistency or conflict between the descriptions, definitions, and/or usage of terms in the accompanying materials of this specification and those described in this specification, the descriptions, definitions, and/or usage of terms in this specification shall prevail.

Finally, it should be understood that the embodiments described in the present disclosure are intended to illustrate the principles of the embodiments of the present disclosure. Other deformations may also belong to the scope of the present disclosure. Thus, as an example, not limited, the alternative configuration of the present disclosure embodiment can be consistent with the teachings of the present disclosure. Accordingly, the embodiments of the present disclosure are not limited to the embodiments of the present disclosure clearly described.

What is claimed is:

1. A method for managing dust pollution in a smart city, which is executed by a management platform, the method comprising:

obtaining, through a sensing network platform, one or more environmental data of an area to be detected and one or more street data associated with the environmental data, the environmental data at least including dust data indicating dust information in the air;

determining, based on the environmental data, whether there is dust pollution in the area to be detected;

in response to determining that there is dust pollution in the area to be detected, determining, based on the environmental data and the street data, a position of at least one dust pollution source and treating the dust pollution; wherein the determining, based on the environmental data and the street data, a position of at least one dust pollution source comprises:

dividing the area to be detected into a plurality of sub-areas;

determining, based on the street data, road network sub-maps of the plurality of sub-areas by the sub-platforms, respectively; each road network sub-map at least including streets of the corresponding sub-area and relationships between the streets; and determining, based on the road network sub-maps and the environmental data, the position of at least one dust pollution source, wherein the determining, based on the road network sub-maps and the environmental data, the position of at least one dust pollution source comprises:

determining, based on the environmental data, one or more target sub-areas with dust pollution from the plurality of sub-areas;

determining, based on the road network sub-maps of the target sub-areas, a target road network map, wherein the target road network map includes streets of the target sub-areas and the relationships between the streets;

extracting a node vector representation of each node and an edge vector representation of each edge from the target road network map; wherein the node represents a street, and the node vector representation at least includes a name, a position and a direction of a street; the edge represents the relationship of the street, the edge vector representation at least includes the relationship between the streets;

extracting the dust data of each node based on the environmental data;

adding the dust data to the node vector representation of each node to obtain a target node vector representation; and determining, according to the target node vector representation and the edge vector representation, the position of the at least one dust pollution source based on a graph neural network;

obtaining, through the sensing network platform, wind direction data at the position of the at least one dust pollution source;

determining, based on the position of the at least one dust pollution source, one or more target streets, wherein the one or more target streets connect to the at least one dust pollution source; and determining, based on inputting the wind direction data, the dust data, the position of the at least one dust pollution source, distance between the at least one dust pollution source and each of the one or more target streets, and weather data to a pollution degree prediction model, degrees of dust pollution of the one or more target streets in a future period.

2. The method of claim 1, wherein treating the dust pollution comprises:

obtaining, through the sensing network platform, positions of a plurality of sweeping vehicle terminals; and allocating, based on the positions of the sweeping vehicle terminals and the degrees of dust pollution of the one or more target streets in the future period, the sweeping vehicle terminals to a target sweeping area.

3. An Internet of Things (IoT) system for managing dust pollution in a smart city, comprising a user platform, a service platform, a management platform, a sensing network platform, and an object platform, wherein the user platform is configured to obtain user's needs;

the service platform is configured to obtain the user's needs from the user platform, and provide, based on the user's needs, services to a user;

the management platform is configured to obtain, through the sensing network platform, one or more environmental data of an area to be detected and one or more street data associated with the environmental data; the environmental data at least including dust data indicating dust information in the air;

determine, based on the environmental data, whether there is dust pollution in the area to be detected;

in response to the determining that there is dust pollution in the area to be detected, determine, based on the environmental data and the street data, a position of at least one dust pollution source and treat the dust pollution; wherein the management platform comprises a plurality of management sub-platforms, a management platform database, and a management information-integrated management platform;

the management platform is further configured to divide the area to be detected into a plurality of sub-areas;

the plurality of management sub-platforms are configured to determine, based on the street data, road network sub-maps of the plurality of sub-areas, respectively; each road network sub-map at least including streets of the corresponding sub-area and relationships between the streets;

the management platform database is configured to obtain the road network sub-maps from the plurality of management sub-platforms;

the management information-integrated management platform is configured to obtain the road network sub-maps from the management platform database, and determine, based on the road network sub-maps and the environmental data, the position of the at least one dust pollution source;

wherein to determine the position of the at least one dust pollution source, the management information-integrated management platform is further configured to determine, based on the environmental data, one or more target sub-areas with dust pollution from the plurality of sub-areas;

determine, based on the road network sub-maps of the target sub-areas, a target road network map, wherein the target road network map includes streets of the target sub-areas and the relationships between the streets;

extract a node vector representation of each node and an edge vector representation of each edge from the target road network map; wherein the node represents a street, and the node vector representation at least includes a name, a position and a direction of a street; the edge represents the relationship of the street, the edge vector representation at least includes the relationship between the streets;

extract the dust data of each node based on the environmental data;

add the dust data to the node vector representation of each node to obtain a target node vector representation; and determine, according to the target node vector representation and the edge vector representation, the position of the at least one dust pollution source based on a graph neural network;

the management platform is further configured to:

obtain, through the sensing network platform, wind direction data at the position of the at least one dust pollution source;

determine, based on the position of the at least one dust pollution source, one or more target streets, wherein the one or more target streets connect to the dust pollution source; and determine, based on inputting the wind direction data, the dust data, the position of the at least one dust pollution source, distance between the dust pollution source and each of the one or more target streets, and weather data to a pollution degree prediction model, degrees of dust pollution of the one or more target streets in a future period;

the sensing network platform is configured to obtain initial environmental data and initial street data from the object platform, and generate, based on the initial environmental data and the initial street data, the environmental data and street data; and the object platform is configured to obtain the initial environmental data and the initial street data.

4. The IoT system of claim 3, wherein the sensing network platform comprises a plurality of sensing sub-platforms and a sensing network platform database;

the sensing network platform database is configured to obtain the initial environmental data and the initial street data from the object platform;

the plurality of sensing sub-platforms are configured to obtain the initial environmental data and the initial street data from the sensing network platform database, and process the initial environmental data and the initial street data to obtain the environmental data and the street data; and the sensing network platform database is further configured to transmit the environmental data and the street data of the plurality of sensing sub-platforms to the management platform.

5. The IoT system of claim 3, wherein the management platform is further configured to:

obtain, through the sensing network platform, positions of a plurality of sweeping vehicle terminals; and allocate, based on the positions of the sweeping vehicle terminals and the degrees of dust pollution of the one or more target streets in the future period, the sweeping vehicle terminals to a target sweeping area.

* * * * *